(12) United States Patent
Lazar (10) Patent No.: US 8,722,358 B2
(45) Date of Patent: May 13, 2014

(54) METHOD FOR OBTAINING STRUCTURAL AND FUNCTIONAL INFORMATION ON PROTEINS, BASED ON POLARIZATION FLUORESCENCE MICROSCOPY

(75) Inventor: Josef Lazar, Pribram (CZ)

(73) Assignee: Centrum Vyzkumu Globalni Zmeny AV CR, v.v.i., Ceske Budejovice (CZ)

(*) Notice: Subject to any disclaimer, the term of this patent is extended or adjusted under 35 U.S.C. 154(b) by 0 days.

(21) Appl. No.: 13/504,112

(22) PCT Filed: Oct. 27, 2010

(86) PCT No.: PCT/CZ2010/000111
§ 371 (c)(1),
(2), (4) Date: Apr. 25, 2012

(87) PCT Pub. No.: WO2011/050760
PCT Pub. Date: May 5, 2011

(65) Prior Publication Data
US 2012/0219983 A1    Aug. 30, 2012

(30) Foreign Application Priority Data
Oct. 27, 2009 (CZ) .................................. 2009-706

(51) Int. Cl.
*G01N 1/30* (2006.01)
*G01N 21/64* (2006.01)
*G02B 21/00* (2006.01)

(52) U.S. Cl.
CPC ........ *G01N 21/6445* (2013.01); *G02B 21/0068* (2013.01); *G01N 21/6428* (2013.01); *G02B 21/0076* (2013.01)
USPC ........................................................ 435/40.5

(58) Field of Classification Search
None
See application file for complete search history.

(56) References Cited

U.S. PATENT DOCUMENTS

| | | | |
|---|---|---|---|
| 5,457,536 A | 10/1995 | Kornfield et al. | |
| 2004/0248144 A1* | 12/2004 | Mir ................................... | 435/6 |

(Continued)

OTHER PUBLICATIONS

Li et al (2007) Micro Res Tech 70: 390-395.*

(Continued)

*Primary Examiner* — Chris L Chin
*Assistant Examiner* — Richard Moerschell
(74) *Attorney, Agent, or Firm* — Workman Nydegger (57) ABSTRACT

The invention pertains to a method of obtaining structural and functional information on proteins, based on polarization fluorescence microscopy, which comprises subjecting a protein tagged with a fluorophore to two- or multi-photon fluorescence microscopy, whereas the observed protein is irradiated with a laser beam with light of at least two different polarizations, which excites the fluorescence of the fluorophore, and wherein information on localization, intensities and polarizations of the fluorescence excited by the different polarizations of the excitation laser beam is used to identify, localize and quantify anisotropy of absorption and/or fluorescence, which information is then used to infer structural and functional properties of proteins. An example of a device for obtaining structural and functional information on proteins, based on polarization fluorescence microscopy, comprises a modulator (P) for rapid modulation of the excitation beam (1) for eliciting two- or multi-photon fluorescence, and a control unit (R), wherein the function of the modulator (P) and control unit (R) is synchronized with scanning of the microscope (M) such that information on fluorescence intensity acquired by the microscope (M) is attributable to a particular polarization state of the excitation beam (1) by virtue of knowing the temporal profile of the polarization modulation of the excitation beam (1) effected by the modulator (P). The method and device of the invention allow determining and monitoring structure and function of proteins, such as membrane proteins, and thereby observing physiological processes in living cells.

12 Claims, 9 Drawing Sheets

(56) References Cited

U.S. PATENT DOCUMENTS

| | | | |
|---|---|---|---|
| 2005/0009109 A1* | 1/2005 | Moerner et al. | 435/7.2 |
| 2005/0031605 A1* | 2/2005 | Bunn et al. | 424/94.4 |
| 2007/0159688 A1* | 7/2007 | Descour et al. | 359/368 |
| 2008/0225906 A1 | 9/2008 | Ishihara et al. | |
| 2010/0267030 A1* | 10/2010 | Smilansky | 435/6 |

OTHER PUBLICATIONS

Li W et al: "Probing rotation dynamics of biomolecules using polarization based fluorescence microscopy", Microscopy Research and Technique 200704 US LNKD—DOI: 10.1002/JEMT.20418, vol. 70, No. 4, Apr. 2007, pp. 390-395.

Steinbach Gabor et al: "Imaging anisotrophy using differential polarization laser scanning confocal microscopy." ACTA Histochemica 2009 LNKD—PUBMED: 19121853, vol. 111, No. 4, Jan. 3, 2009, pp. 316-325.

Diaspro A et al: "Two-Photon Microscopy and Spectroscopy based on a compact confocal scanning head", Journal of Biomedical Optics, Spie-International Society for Optical Engineering, US, vol. 6, No. 3, Jul. 1, 2001, pp. 300-310.

International Search Report from International Application No. PCT/CZ2010/000111 dated Feb. 23, 2011.

\* cited by examiner

METHOD FOR OBTAINING STRUCTURAL AND FUNCTIONAL INFORMATION ON PROTEINS, BASED ON POLARIZATION FLUORESCENCE MICROSCOPY

This application is a U.S. nationalization of PCT/CZ2010/000111, which was filed 27 Oct. 2010 and entitled "A METHOD FOR OBTAINING STRUCTURAL AND FUNCTIONAL INFORMATION ON PROTEINS, BASED ON POLARIZATION FLUORESCENCE MICROSCOPY, AND A DEVICE IMPLEMENTING SAID METHOD." PCT/CZ2010/000111 claims the benefit of and priority to Czech patent application PV 2009-706, which was filed 27 Oct. 2009. The above listed applications are incorporated herein by reference in their entireties.

FIELD OF THE INVENTION

The invention described herein concerns polarization microscopy, specifically in two- and multi-photon arrangement. The invention is a method for obtaining structural and functional information about properties of proteins, preferably proteins in live cells, and a device implementing said method. The method and device allow, using two-photon or multi-photon polarization fluorescence microscopy, to determine and monitor structure and function of proteins, for example membrane proteins, and in doing so, observe physiological processes in live cells.

BACKGROUND OF THE INVENTION

Proteins in live cells can be studied, after being tagged by an optically observable label, by optical methods. Often, the optically observable tag used is a fluorescent protein. Presence of a fluorescent protein tag then allows observations of presence and spatial distribution of the studied protein in live cells, using a fluorescence microscope. However, presence and spatial distribution of fluorescence alone generally do not allow monitoring functional activity of the studied protein, such as whether a receptor protein is activated, an ion channel open or closed, a transporter protein transporting, etc.

Our ability to observe functional activity of proteins in living cells is very limited. Available optical methods generally rely on one or more of three basic principles: 1) production of an optically detectable species through activation of transcription; 2) fluorescence lifetime imaging (FLIM); and 3) fluorescence resonance energy transfer (FRET). Although useful, all of these methods have their limitations. Transcription activation takes minutes to hours, which is too long to observe many systems. FLIM requires expensive equipment, is not very sensitive, and FLIM data cannot be interpreted in terms of protein structure. FRET requires two optically active molecules (e.g. fluorescent proteins), which often negatively affects function of the system studied. Furthermore, the observed transfer of fluorescence energy (FRET signal) is only a fraction of the total fluorescence, and so is often hard to detect on the background fluorescence from the two present fluorescent moieties.

SUMMARY OF THE INVENTION

Limitations of the current methods are overcome by a method and a device for two-photon (or multi-photon) polarization fluorescence microscopy, which allow obtaining structural information on proteins, preferably membrane proteins, and observing physiological processes (on cellular and subcellular level) in which these proteins participate. Generally, polarization fluorescence microscopy utilizes the fact that properties of many fluorophores (including those of fluorescent proteins) are anisotropic, and therefore the processes of absorption and emission of light depend on the orientation of the fluorophore. Both calculations and experiments carried out by the inventor have shown that if a fluorescent label (such as a fluorescent protein) is attached to a suitable support (a membrane protein, a cytoskeletal protein, or a protein immobilized in another way, such as by immobilization through a design), restriction of free rotation is often sufficient to allow, under suitable experimental arrangement, observation of anisotropic fluorescence properties (in both emission and absorption) even when the immobilization support (such as cell membrane or cytoskeleton) is not smooth and the link between the fluorescent tag (fluorescent protein) and the studied protein is flexible. In soluble proteins, the orientation of the fluorescent tag is random, and the anisotropic fluorophore properties, present when excitation beam of various polarizations is used, will not be manifested in the amount of the emitted fluorescence, however, they will affect the polarization and direction of emission. Thus, anisotropic properties of fluorophores can be observed under many different circumstances, and they can, in principle, be used to monitor physiological processes in living cells.

Even though anisotropic fluorescence properties are, in principle, observable with single-photon excitation, multi-photon excitation (in an example, two-photon excitation) has significant advantages: higher sensitivity of absorption to fluorophore orientation (fourth power of the cosine of the angle between the polarization o the excitation light and orientation of the transition dipole moment, compared to second power of this cosine for single-photon excitation), and excitation of fluorescence only in the vicinity of the objective focal plane (where the polarization of the excitation beam is well defined), along with good optical resolution along the vertical axis. These advantages are critical for successful observation of small changes in anisotropy associated with many physiological processes. The observed anisotropy can be used to infer information about orientation of the fluorescent tag (fluorescent protein) in the observed cells, restriction of free rotation, speed of molecular rotation (and therefore the molecular size or interactions with other molecules), changes in excited state lifetime (and therefore the environment in the vicinity of the fluorophore, including proximity of a suitable acceptor for homo- or heteromolecular FRET), and other properties. Changes in anisotropy can also be used to monitor physiological processes such as activation of G-proteins, activation of protein kinases, changes in intracellular calcium concentration, cell membrane voltage, interactions of cytoplasmatic proteins with membranes and other proteins, and other processes.

In a preferred embodiment of the invention, microscopic imaging of the studied cells is carried out using at least two different (preferably mutually perpendicular linear) orientations of polarization of a polarized light beam, preferably a laser beam. The imaging experiment is preferably carried out so that in between acquisitions of individual images, the linear polarization of the excitation laser beam (which may be modified beforehand, such as by a polarizing beamsplitter) is changed by a half-wave plate, polarizer, or another device. An image is understood to be a semblance of the microscopically observed object, in a digital form (for example in the TIFF format) of a matrix composed of elementary units termed pixels. Each pixel then is a graphical representation of measured amount of fluorescence, originating in a precisely defined part of the observed sample, during a precisely defined time interval. A person skilled in the art would be aware that the data on the measured amount of fluorescence can also be represented in other ways, such as in the form of a graph or a table.

In order to obtain information about relative changes in fluorescence intensities correlating with changes in polarization of the excitation beam, the acquired images are compared, preferably by dividing values describing fluorescence intensities in one image by corresponding values in another image.

Since living cells undergo microscopic motions, a precise analysis of images acquired with different polarizations requires that these images be of high quality, and acquired over as short a time span as possible. Rapid acquisition of images with different polarizations also allows monitoring of rapid physiological processes, such as changes in calcium concentrations, or changes in cell membrane voltage.

A device for multi-photon, preferably two-photon, polarization fluorescence and higher harmonic emission microscopy that allows rapid acquisition of images with different polarizations of excitation light, and carrying out the method described herein, is another subject of this invention. Preferably, this device is in the form of a module attachable to a laser scanning microscope that allows synchronization with external or internal devices, and is suitable, in terms of quality and quantity of available excitation and observation capabilities, for observation of fluorescence of biological samples. The device comprises an excitation laser beam polarization modulator, synchronized with the microscope by a control unit and timing signals. In order to measure polarization of emitted fluorescence, the device can be preferably supplemented by a polarizer or a polarizing beam splitter inserted between the observed sample and the fluorescence detector.

The device functions by changing the polarization of the laser beam in synchrony with operation of the microscope so that one image (termed mixed image) acquired by the microscope comprises separate parts (preferably, pixels), each obtained with one of several (in an example, two) different polarizations of the excitation beam. In reality, each part of the mixed image is acquired with predominantly one polarization of the excitation beam, due to polarization distortion by optical components and due to delays in detector response, which can be mathematically corrected, as shown below. The mixed image is then processed (deconvolved) into individual images, each acquired with a different polarization of the excitation beam. These images can then be further processed and analyzed in the same fashion as a sequence of images acquired sequentially with different polarizations.

The method of deconvolution of the mixed image is also a part of the present invention. It comprises two basic steps. In Step 1, signal (fluorescence) elicited by individual polarizations (polarization #1, polarization #2, . . . ) of the excitation beam is identified in the mixed image. In Step 2, for each of the used polarizations, a separate image is created from the signal elicited by that polarization of the excitation beam. The result is a set of two or more images, each containing only signal elicited by one polarization of the excitation beam.

In a preferred embodiment, consecutive pixels of the mixed image contain information on fluorescence excited with consecutive polarizations of the excitation beam. For example, each odd-numbered pixel contains information on fluorescence excited with the excitation beam polarized horizontally; each even-numbered pixel contains information on fluorescence excited with the excitation beam polarized vertically. Step 1 of mixed image deconvolution then comprises identifying odd (or even) numbered pixels of each row of the mixed image. In Step 2, all odd-numbered pixels of all rows of the mixed image are assembled to create an image containing signal excited using horizontally polarized excitation laser beam; all even-numbered pixels of all rows of the mixed image are assembled to create an image containing signal excited using horizontally polarized excitation laser beam. Thus, each of the resulting images contains only information obtained with one polarization of the excitation beam.

Preferably, Step 1 of the method of deconvolution of the mixed image may include steps compensating for delayed response of detectors or other undesirable properties of the microscopic system. Step 2 may preferably include methods compensating for bleaching or other fluorophore changes. The device and method for polarization fluorescence microscopy described herein then allow accurate, almost simultaneous microscopic observations of fluorescence with two or more polarizations of the excitation beam, and analysis of the acquired information for the purpose of observing and monitoring structural properties of proteins, interactions of proteins (or other fluorescent molecules) with other molecules and with the surrounding environment, and for monitoring protein function.

A preferred embodiment of the device according to the invention is described in detail in Example 1.

The method of the invention, using the device of the invention, was demonstrated by observations of a green fluorescent protein (GFP) modified so that when expressed in cells (such as HEK293 cells), it will bind to the cell membrane (Example 2).

Obtaining protein structure information was demonstrated on a G-protein tagged by a cyan fluorescent protein (CFP), on a protein sensitive to calcium ion concentration, on a protein sensitive to cell membrane voltage, on receptor proteins, and on a protein attached to the cytoskeleton (Example 3). These examples show that the method of the invention has yielded quantitative information on fluorescent protein orientation.

The method of the invention also allows monitoring changes in protein structure as a result of protein function, and therefore monitoring of protein function. This is illustrated on an example of G-proteins and protein kinase C (Example 4).

The method and device of the invention allow monitoring of fluorescence polarization as a reporter of interactions of a fluorescently tagged cytoplasmic protein with other molecules, as illustrated in Example 5 on a cytoplasmic yellow fluorescent protein (YFP) expressed in HEK293 cells.

The subject-matter of the invention is a method of obtaining structural and functional information on proteins, based on polarization fluorescence microscopy, comprising I) attaching a fluorophore to the protein of interest, II) subjecting the fluorophore-attached protein to two- or multi-photon fluorescence microscopy, whereas the fluorophore-attached protein is irradiated by a laser beam with polarized light of at least two distinct polarizations, which excites fluorescence of the fluorophore, III) collecting information on localization, intensity and/or polarization of fluorescence obtained with distinct polarizations of the excitation laser beam, IV) using information on localization, intensity and/or polarization of fluorescence obtained with distinct polarizations of the excitation laser beam to identify and localize anisotropy of absorption and/or fluorescence, and V) ascertaining structural and functional properties of proteins from localization and quantitation of anisotropy of absorption and/or fluorescence.

In a preferred method of the invention, information on localization and intensity of fluorescence excited with distinct polarizations of the excitation beam is obtained in the form of a mixed image, containing in its distinct parts information on intensity of fluorescence excited by distinct polarizations of the excitation laser beam.

In a preferred method of the invention, processing of the mixed image comprises steps in which a) for each part of the mixed image, signal excited by individual polarizations of the excitation beam is identified, and b) for each polarization of the excitation beam, a separate image is created, containing only signal excited by that polarization.

In another preferred method, the distinct parts of the mixed image, containing fluorescence intensities excited by distinct polarizations of the excitation laser beam, are pixels.

In a preferred method of the invention, two distinct polarizations of light of the excitation laser beam are used.

In another preferred method, the two distinct polarizations of the excitation laser beam are linear, in mutually perpendicular directions.

Preferably, the mixed image obtained by the method of invention contains in odd-numbered pixels intensities of fluorescence excited by one of the two polarizations used, and in even-numbered pixels intensities of fluorescence excited by the other of the two polarizations used.

In another embodiment, anisotropy of fluorescence for individual pixels is preferably determined by calculating a ratio of intensity of fluorescence excited by one polarization of the excitation laser beam and intensity of fluorescence excited by the other polarization of the excitation laser beam.

Preferably, the protein being studied is a membrane protein.

In another preferred embodiment, the protein being studied is a G-protein.

In yet another preferred embodiment of the method of the invention, the protein being studied is a protein sensitive to calcium ion concentration.

In another preferred embodiment, the protein being studied is a protein sensitive to cell membrane voltage.

Also preferably, the protein being studied is a receptor protein.

In yet another embodiment, the protein being studied is an enzyme.

In another preferred embodiment, the protein being studied is a cytoplasmic protein.

Also preferably, the protein being studied is a protein attached to the cytoskeleton.

Another subject-matter of the invention is a device for obtaining structural and functional information on proteins, based on polarization fluorescence microscopy, which comprises a modulator for rapid modulation of the polarization of the excitation beam used for excitation of two- or multi-photon fluorescence, and a control unit, the function of the modulator and the control unit being synchronized with scanning of the microscope, so that information on fluorescence intensity acquired by the microscope can be attributed to individual polarization states of the excitation beam by virtue of knowing the temporal profile of the excitation beam polarization modulation effected by the modulator.

In a preferred embodiment of the device, a polarizer is placed in the microscope, in front of the fluorescence detector.

In another preferred embodiment, the modulator comprises a Pockels cell, driven by a high-voltage driver that modulates, under the command of low voltage pulses generated by generator of low voltage pulses, high voltage provided by a high voltage power supply.

In yet another preferred embodiment of the device of the invention, the central processing unit synchronizes function of the polarization modulator and the fluorescence microscope by virtue of timing signals generated by the data acquisition device of the microscope.

In another preferred embodiment, the control unit carries out the method of the invention in an automated fashion.

Preferably, the control unit is in the form of a computer, and comprises implemented steps of the method for obtaining structural and functional information on proteins of the invention.

Preferably, the control unit in the form of a computer comprises an implementation of steps for ascertaining and localizing anisotropy of fluorescence according to the method of the invention.

BRIEF DESCRIPTION OF THE FIGURES

FIG. 6. Examples of applications of the method of two-photon polarization fluorescence microscopy for observing protein structure. a) A cell expressing a Gαi2-YFP G-protein subunit, in absence of Gβ1 and Gγ2 subunits, shows no absorption anisotropy. b) A cell expressing the Gαi2-YFP subunit along with Gβ1 and Gγ2 subunits shows absorption anisotropy indicative of orientation of the fluorophore close to parallel to the cell membrane. c) The cyan fluorescent protein present in the calcium ion sensor lynD3cpV shows absorption anisotropy indicative of orientation of the fluorophore close to perpendicular to the cell membrane. d) The yellow fluorescent protein present in the calcium ion sensor lynD3cpV shows no observable absorption anisotropy, indicative of disordered fluorophore orientation with respect to the cell membrane. e) The cyan fluorescent protein (a part of VSFP3.1, a fluorescent probe of cell membrane voltage) shows absorption anisotropy indicative of orientation of the fluorophore close to parallel to the cell membrane. f) The green fluorescent protein attached to the glutamate receptor protein mGluR1 shows very strong absorption anisotropy indicative of fluorophore orientation almost exactly parallel to the cell membrane. g) The cyan fluorescent protein attached to the α2-adrenergic receptor protein shows absorption anisotropy weaker than in e), indicative of orientation of the fluorophore close to parallel to the cell membrane. h) The yellow fluorescent protein attached to the a2-adenosine receptor protein shows absorption anisotropy indicative of orientation of the fluorophore close to perpendicular to the cell membrane. i) The green fluorescent protein attached to the cytoskeletal protein tau shows anisotropy indicative of fluorophore orientation close to parallel to the orientation of microtubules.

EXAMPLES

It is understood that the specific examples of embodiments and uses of the invention described and illustrated below are meant to illustrate preferred embodiments by example, and should in no way be understood as limitations.

Example 1

Figure 1:
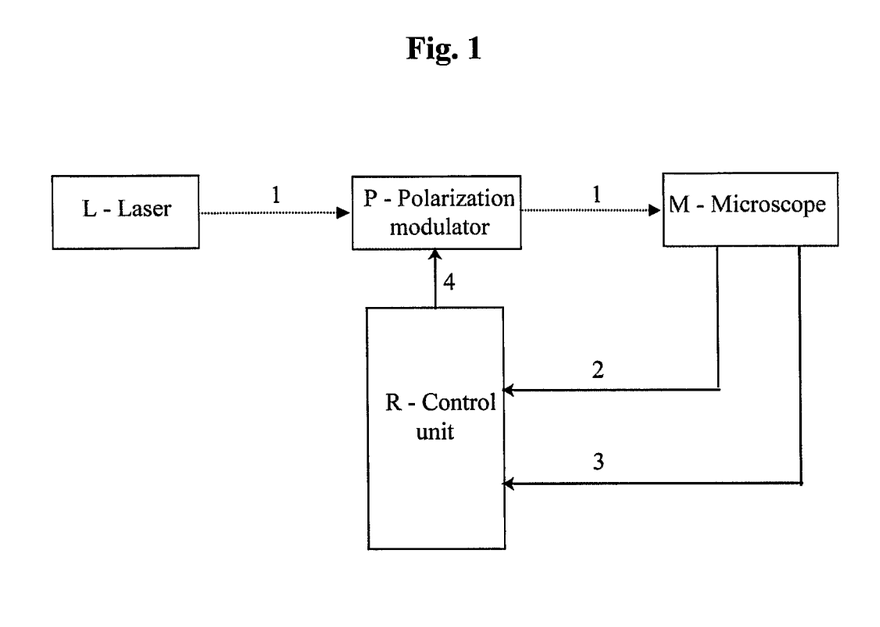
FIG. 1. Schematic drawing of a principle of a device for obtaining structural and functional information on proteins using polarization fluorescence microscopy.

A Device for Obtaining Structural and Functional Information About Proteins, Based on Polarization Fluorescence Microscopy A device for carrying out polarization fluorescence microscopy, in principle illustrated in FIG. 1, has been created. The device comprises, as major components, a polarization modulator P acting on an excitation beam 1 emitted by a laser L, synchronized with a scanning fluorescence microscope M by a control unit R using timing signals 2 and 4.

A device (shown in FIG. 2) has been designed to create a linearly polarized excitation laser beam 1 with direction of polarization modulated in synchrony with scanning of the microscope M. This was achieved by using a polarization modulator P consisting of a Pockels cell C (RTP-3-20-AR800-1000, Leysop Inc., United Kingdom) under the control of a high-voltage driver D (model B2, BME Bergmann GmbH, Germany). Driver D modulates high voltage 6 (0-1.2 kV), generated by a high voltage power supply Z (model HV, BME Bergmann GmbH, Germany), under the command of low voltage (TTL) pulses 5 generated by a pulse generator G (model SP05, BME Bergmann GmbH, Germany). Synchronization of the polarization modulator P with the microscope M (laser scanning microscope iMic, Till Photonics GmbH, Germany, equipped with a two-photon laser Chameleon Ultra II (Coherent Inc., Great Britain) and photomultiplier tube detectors of fluorescence/second harmonic emission Hamamatsu) is accomplished by a central control unit R (based on a signal delay card G02, BME Bergmann GmbH, Germany) using timing signals 2, 4. The timing signals used are the 8 MHz timing pulses sent by the microscope's data acquisition device (based on a data acquisition card NI PCI-6111, National Instruments Inc., USA). The described polarization module is triggered by a low voltage signal sent by the microscope M during scanning of each image line. The frequency of polarization modulation of the excitation beam 1 is set using information about duration of acquisition of individual pixels by the microscope M, provided by the software that drives the microscope M. In an example, the acquired microscopy data 3 (including microscopic images and accompanying information about duration of acquisition of individual pixels, about duration of delays between acquisitions of individual pixel rows, about the position of the sample and of the laser beam, about the excitation light wavelength and intensity) are processed by the control unit R. In this arrangement, the Pockels cell C alternates the polarization of the excitation beam 1 such that consecutive pixels created by the microscope M represent fluorescence excited by different polarization states of the excitation beam 1.

Figure 2:
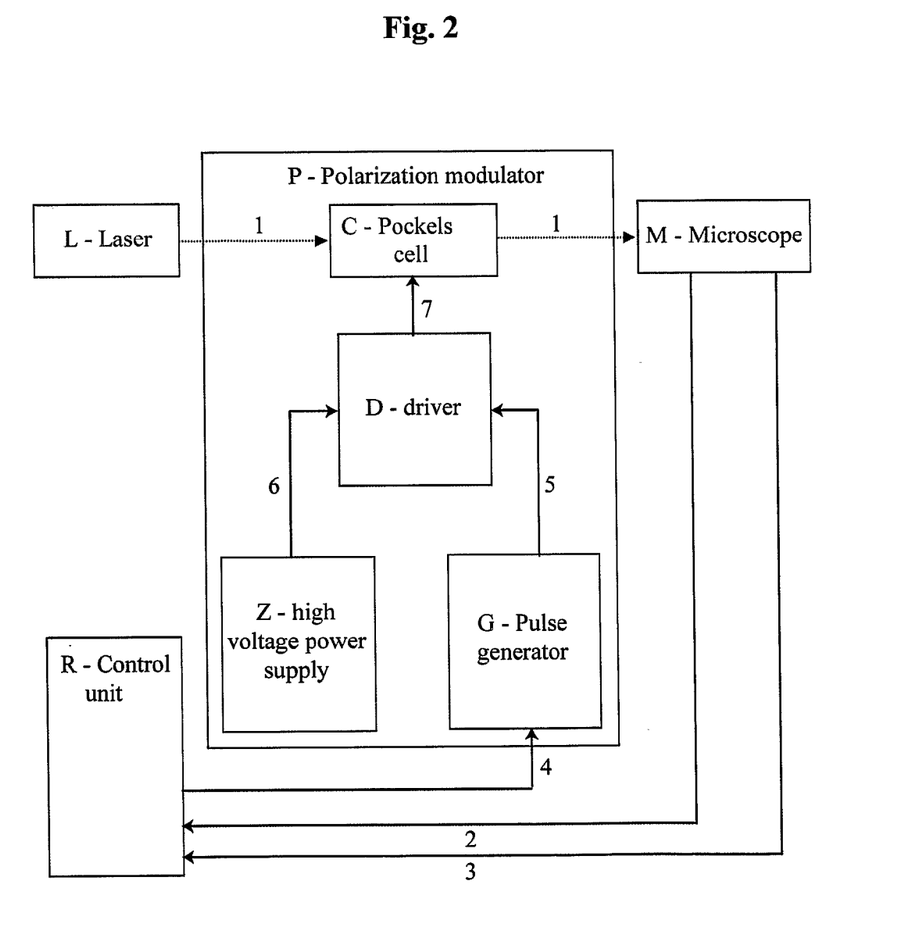
FIG. 2. Example of a preferred embodiment of a device for obtaining structural and functional information on proteins using polarization fluorescence microscopy FIG. 3. Illustration of the function of a device for obtaining structural and functional information on proteins using two-photon polarization fluorescence microscopy. a) Experimental setup, identical to that in FIG. 1, except for a polarizing beamsplitter (B) inserted in the laser beam for purposes of function illustration. b) Image of a homogeneously fluorescent object acquired by the system shown in FIG. 3a. Each pixel corresponds to a time interval of 0.25 μs.
Figure 3:
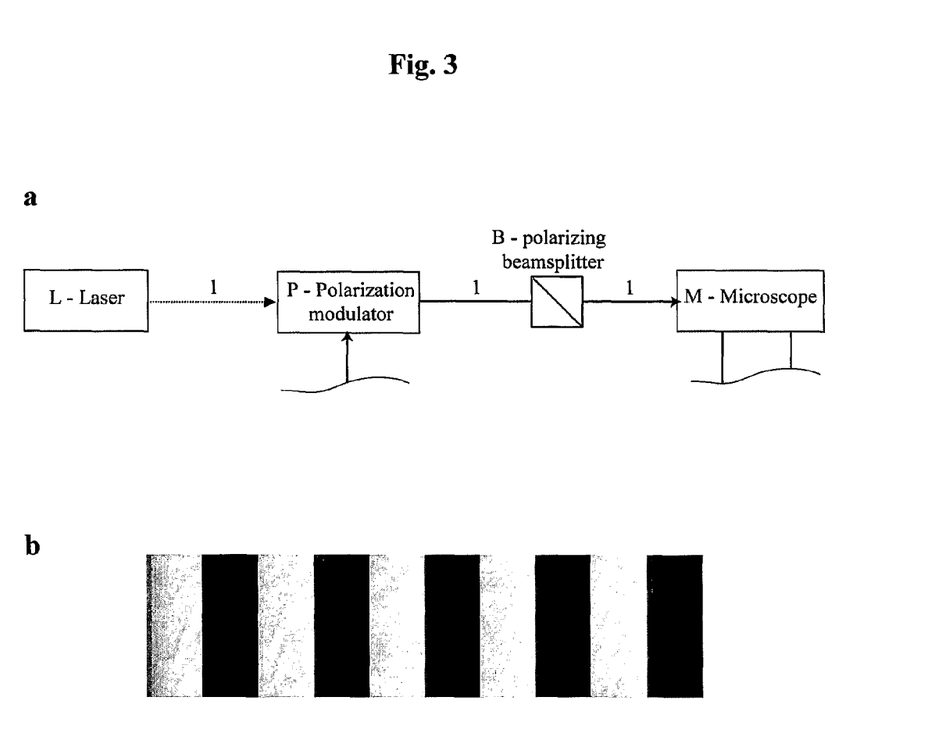

Function of the described device (FIG. 2) in polarization fluorescence microscopy is illustrated in FIG. 3. To illustrate the function of the device, a polarization beamsplitter B (reflecting horizontally polarized light away from the microscope M) was placed in the excitation beam 1 after the polarization modulator P (FIG. 3a). Polarization of the excitation beam 1 was alternated between horizontal and vertical, with a period of 2.5 μs. The period of acquisition of a single pixel by the microscope was 0.25 μs. FIG. 3b shows an image of a homogeneously fluorescent object (a fluorescent plastic plate) acquired by the system illustrated in FIG. 3a. Synchronization of laser beam 1 polarization modulation with scanning by the microscope M is apparent. Had the fluorescence detectors used responded without delays and persistence, the acquired image would have consisted of homogeneously white and black stripes. The discernible shades of grey are caused by delays and persistence in microscope detector response (i.e., fluorescence elicited by vertically polarized laser beam is still being reported by the detectors during periods when the laser beam is already polarized horizontally, and vice versa). Delays and persistence in detector responses are typical of the sensitive photomultiplier-based detectors used as fluorescence detectors in many microscopes.

Example 2

Obtaining Structural and Functional Information About a Modified GFP Using Polarization Fluorescence Microscopy and the Device of Example 1

Figure 4:
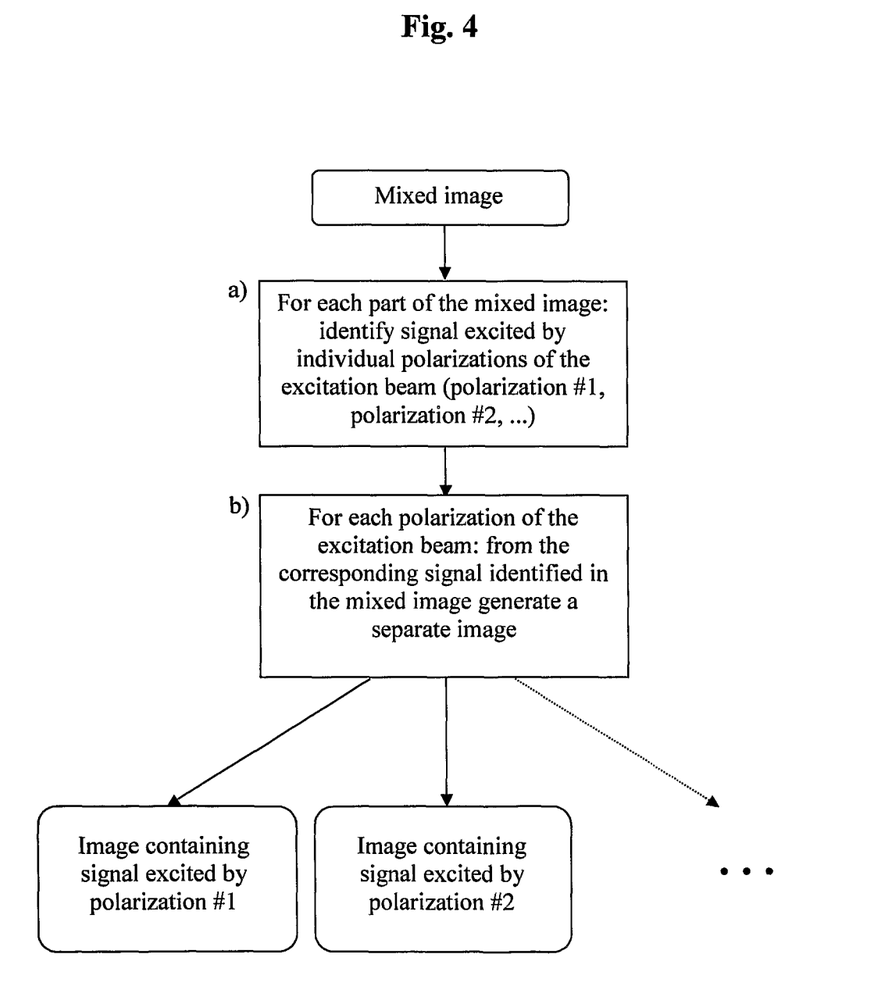
FIG. 4. Schematic drawing of the method of deconvolution of a mixed image.
Figure 5:
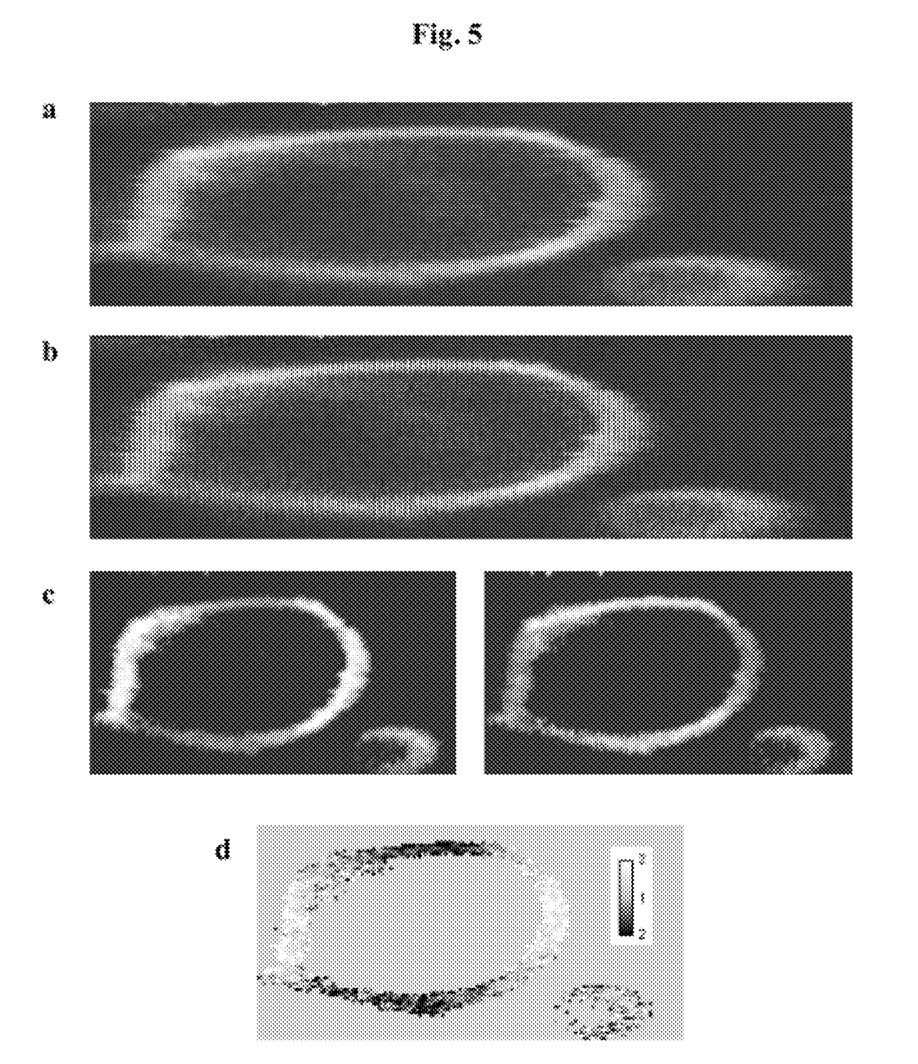
FIG. 5. A mammalian cell producing a membrane protein tagged with a fluorescent protein, exhibiting pronounced absorption anisotropy, imaged using a device for rapid polarization modulation in two-photon polarization fluorescence microscopy. a) A mixed image, in which in each row, odd-numbered pixels correspond to periods during which the excitation beam was polarized vertically, and even-numbered pixels correspond to periods during which the excitation beam was polarized horizontally. b) A mixed image after adjustments for delay and persistence of detector response. c) Images containing signal elicited by individual polarizations of the excitation beam. d) An example of further processing of images in FIG. 5c.

The device of Example 1 was used to acquire an image containing different parts (pixels) acquired with different polarizations of the excitation beam, i.e., a mixed image. The mixed image was deconvolved into separate individual images, each acquired with a different polarization of the excitation beam, in a manner schematically shown in FIG. 4. The result is illustrated in FIG. 5. Steps were taken during processing of the mixed image to account for delays in detector response and other factors. This was done by measuring the temporal response profile of the detectors used, and ascertaining what percentage of the signal (fluorescence) excited during a period of one polarization of the excitation beam is being reported in a pixel acquired during that period, and what percentage is being reported later. During deconvolution of the mixed image, the intensity of a first pixel was then used to calculate how much fluorescence excited with the beam polarized one way is being reported in the first pixel, and how much is being reported in the following pixels. The intensity of the first pixel was then correspondingly increased, while the intensity of the following pixels was decreased. Other pixels were then processed in the same fashion in a consecutive order.

An example of a mixed image is presented in FIG. 5a, depicting a mammalian cell of the HEK293 line, into which a gene was inserted, encoding a green fluorescent protein modified so that the resulting protein would be attached to the cell membrane in a well-defined orientation (doubly lipidated eGFP, prepared by dr. Gero Miesenboeck, Oxford University, Great Britain). The cell was imaged using a two-photon laser scanning microscope iMic (Till Photonics GmbH, Germany), equipped with the above described prototype of the device of the invention (FIG. 2). In each row of the image, odd-numbered pixels were recorded during periods of vertical polarization of the excitation laser beam; even-numbered pixels were recorded during periods of horizontal polarization of the excitation laser beam. Polarization of the laser beam was alternated with a period of 2.5 µs.

In Step 1 of the method of deconvolution of the mixed image, signal elicited by each polarization of the excitation beam was identified for each part of the mixed image. Had the response of the fluorescence detectors been immediate, signal (fluorescence) excited by vertically polarized laser beam would have been present solely in odd numbered pixels of each row of the mixed image. However, the response of the detectors used (photomultipliers) generally shows delays and persistence. Therefore, fluorescence excited by the laser beam of a particular polarization elicits detector signal even after a change in polarization of the excitation beam. Our measurements of response of detectors used in this example had indicated that about 31% of fluorescence excited during acquisition of a particular pixel was reported by detectors during acquisition of the following pixel by the microscope.

In order to identify signal (fluorescence) excited by individual polarizations of the excitation laser beam, the following procedure was followed for each row of the mixed image. The value of intensity of the first pixel (for example, 1000) was increased by 31% (that is, by 310, to 1310). The value of the second pixel (for example, 900) was decreased by the same amount (to 590). The value of the second pixel was then increased by 31% (by 183, to 773). The value of the third pixel (for example, 1050) was decreased by this amount (to 867), followed by an increase by 31% (that is, by 269, to 1136). This process was sequentially used for each pixel within a row, and for each row of a mixed image. Each line of the resulting image (FIG. 5b) is composed of pixels containing signal excited by vertically (odd-numbered pixels) and horizontally (even-numbered pixels) polarized excitation laser beam. In this manner, signal elicited by each polarization of the excitation beam was identified (that is, quantified and spatially localized), as is the goal of Step 1 of the method of mixed image deconvolution.

In step 2 of the method of mixed image deconvolution, a separate image (FIG. 5c) was created for each one of the two polarizations (vertical and horizontal) of the excitation laser beam used, from signal excited by the particular polarization, in the following fashion. The image corresponding to vertical polarization of the excitation beam (FIG. 5c, right panel) was assembled from odd-numbered pixels (containing signal excited by vertically polarized excitation laser beam) of each row. The image corresponding to horizontal polarization of the excitation beam (FIG. 5c, left panel) was assembled from even-numbered pixels (containing signal excited by horizontally polarized excitation laser beam) of each row.

Images thus created were used for measurements and monitoring of anisotropic fluorescence properties. The ratio between intensity of fluorescence excited by one polarization of the excitation laser beam and intensity of fluorescence excited by the other polarization of the excitation laser beam was calculated. In this calculation, for each position within the observed sample, the intensity of fluorescence excited by vertical polarization of the laser beam was divided by the fluorescence intensity excited by horizontal polarization of the laser beam. A logarithm of this ratio was calculated and presented in the form of an image, such that the values of the logarithm are expressed as shades of grey (FIG. 5d). Excess of light shades in horizontally oriented parts of a cell outline, combined with excess of dark shades in vertically oriented parts of a cell outline (or vice versa) indicate presence of anisotropy in fluorophore absorption. Presence and size of this anisotropy are then indicative of orientation of the fluorophore with respect to cellular structures, such as the cell membrane, and can be used for monitoring of biological processes.

Preferably, visualization of anisotropy can also be carried out so that for each location within the observed sample, the logarithm of the ratio of fluorescence intensities excited by individual polarizations of the laser beam is presented in the form of an image, such that the size of the logarithm determines the hue on a colour scale (e.g. red-yellow-green), and the total observed fluorescence intensity determines brightness of the image. Excess of one colour in horizontally oriented sections of the cell outline, combined with excess of another colour in vertically oriented sections of the cell outline then indicate presence of anisotropy in absorption by a fluorophore.

The extent of observed anisotropy in a particular part of a cell outline can be compared to anisotropy predicted for the same part of the cell outline for various fluorophore orientations (described, for example, by a mean fluorophore tilt angle and a width of distribution of the tilt angle among present molecules). Identification of a best fit between mathematical prediction and experimental data yields quantitative information on fluorophore orientation (and therefore on protein structure) in living cells.

Example 3

Monitoring and Determination of Protein Structure

Figure 6:
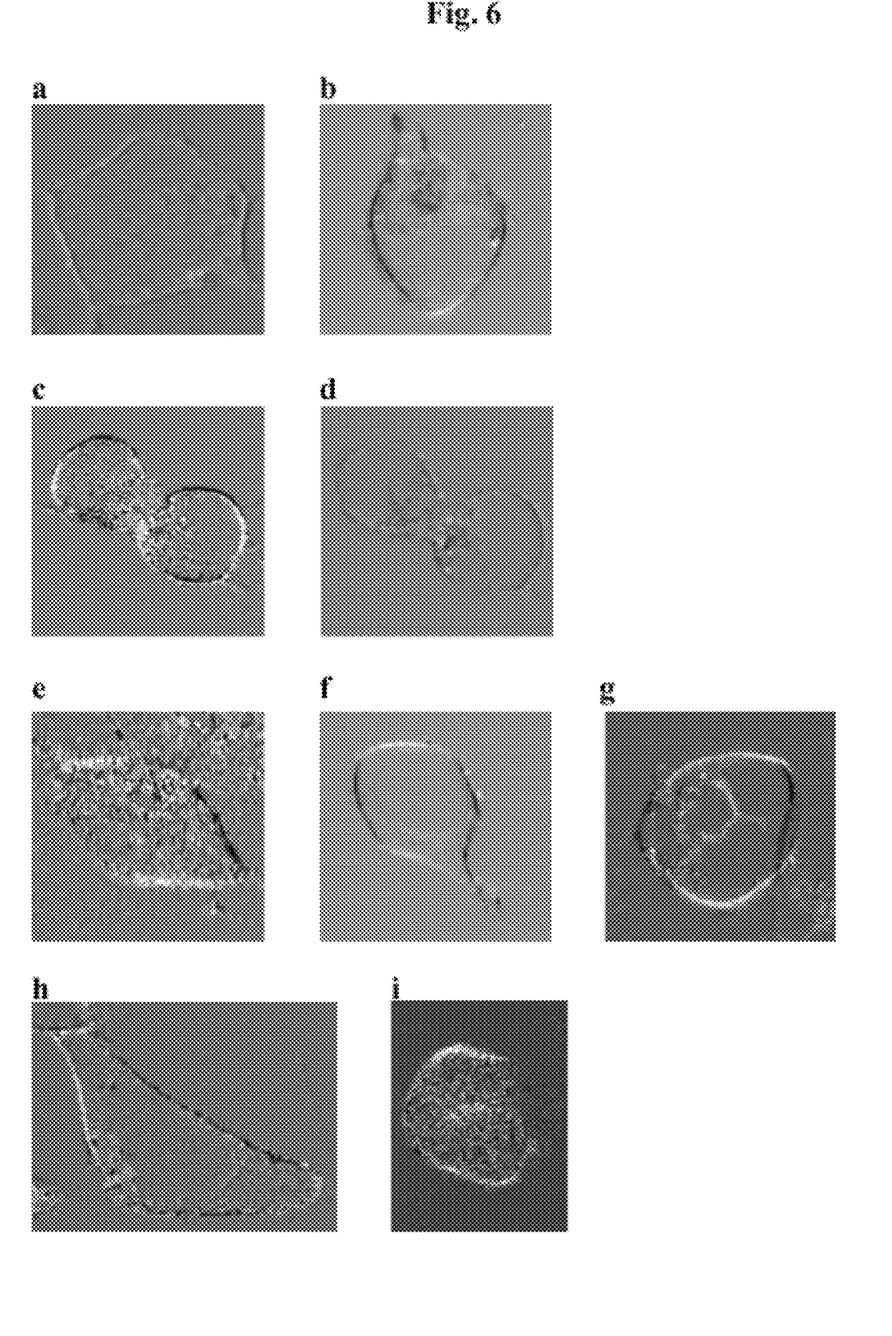

The method and device for two-photon polarization microscopy of the invention have been used to determine and monitor structure of G-proteins, structure of a protein sensitive to calcium ion concentration, a protein sensitive to membrane voltage, receptor proteins, and a cytoskeleton attached protein (FIG. 6).

Example 3a

Structure of G-Proteins

G-proteins typically consist of three subunits, Gα, Gβ, and Gγ, which may, in live cells, interact with each other. The function of 0-proteins is transmission and amplification of signals from various receptor proteins. Ability to directly optically monitor G-protein activation caused by activation of a particular receptor protein can be used to improve our understanding of mechanisms of cell signalling, but also for discovering pharmacologically active compounds acting on G-proteins or G-protein coupled receptors.

Our observations of subunits Gαi2-CFP, Gβ1, and Gγ2 have shown that the cyan fluorescent protein (CFP) attached to the Gαi2 subunit does not exhibit observable absorption anisotropy if this subunit is expressed in mammalian cells without co-expression of both Gβ1 and Gβ2 (FIG. 6a). A likely explanation of the absence of anisotropy is disordered orientation of the present CFP molecules. This can be caused by disordered orientation of the Gα subunit itself.

If, however, all three subunits (Gαi2-CFP, Gβ1 and Gγ2) are co-expressed in one cell, anisotropy in CFP absorption can be observed (FIG. 6b). This anisotropy is manifested, in images processed similarly to the one shown in FIG. 5, as an excess of dark shades in vertically oriented parts of the cell outline, and an excess of light shades in horizontally oriented parts of the cell outline. This excess of fluorescence excited by horizontally polarized light over fluorescence excited by vertically polarized light in parts of the cell outline oriented vertically (and vice versa) shows that the transition dipole moment of fluorophore excitation (proximal to the long axis of the fluorophore) is, in live cells, oriented close to parallel to the cell membrane.

The described method of two-photon polarization microscopy has therefore been used to determine that in absence of Gβ and Gγ subunits, the orientation of the fluorescent protein attached to Gαi2 is likely disordered. In contrast, in presence of subunits Gβ1 and Gγ2, the orientation of the fluorescent protein is rather well defined, such that the long axis of the fluorophore is close to parallel with the cell membrane. The method of the invention therefore allows observing the interaction between Gαi2-CFP, Gβ1 and Gγ2, and inferring information on structure of proteins in living cells. The method described herein also allows monitoring expression of the Gβ1 and Gγ2 subunits, which are not fluorescently labeled, but whose simultaneous presence will manifest itself by presence of anisotropy of the CFP absorption of the Gαi2-CFP construct. The method described herein also allows monitoring changes in structure and interactions between the individual subunits, which are caused by activation/inactivation (that is, by function) of the observed G-protein (Example 4).

Example 3b

Structure of a Protein Sensitive to Calcium Ions

Cytoplasmic concentration of calcium ions is a hallmark of activation of various cell signalling cascades. In order to monitor calcium concentration, a number of probes based on fluorescent proteins have been developed. One of these probes is termed lynD3cpV (developed by R. Tsien, University of California, San Diego, USA). This particular probe employs FRET between a cyan fluorescent protein, which is anchored to the cell membrane, and a yellow fluorescent protein ('circularly permuted Venus', cpV). Both fluorescent proteins are linked through a calcium ion sensing domain. Changes in calcium ion concentrations lead to structural changes in this domain, which cause changes in mutual orientation of the fluorescent proteins, and therefore changes in FRET.

Figure 9:
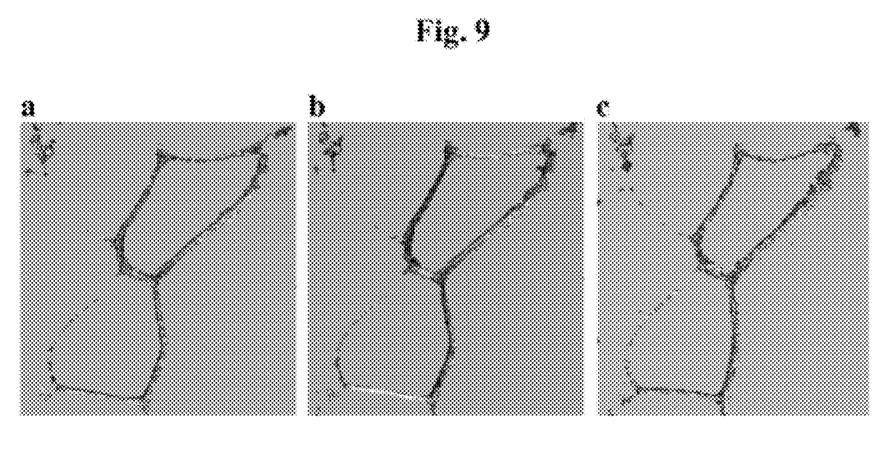
FIG. 9. An example of applications of the method of two-photon polarization fluorescence microscopy to monitoring intracellular calcium concentration. a) A cell expressing a calcium sensitive protein lynD3cpV, in a resting state, showing no absorption anisotropy in the yellow fluorescent protein present. b) The same cell as in a), but with an elevated intracellular calcium concentration, shows absorption anisotropy indicative of fluorophore of the yellow fluorescent protein being close to parallel to the cell membrane. c) The same cell as in a) and b), but after return of intracellular calcium concentration back to resting levels. No absorption anisotropy is visible.

The method of two-photon polarization microscopy described herein has been used to establish that in the resting state, the cyan fluorescent protein is attached to the cell membrane such that the long axis of its fluorophore is close to perpendicular to the membrane (FIG. 6c). The yellow fluorescent protein does not show absorption anisotropy in a resting state (FIG. 6d, FIG. 9a), and is therefore likely in a disordered orientation. Changes in calcium ion concentration will lead to changes in orientation in the two fluorescent proteins, which can be observed by the method of two-photon polarization microscopy described herein. Specifically, an increase in intracellular calcium concentration (such as by exposure of cells to ATP or histamine) leads to a conformational change in lynD3cpV leading to appearance of absorption anisotropy in the yellow fluorescent protein moiety (FIG. 9b), with the long axis of the fluorophore becoming close to parallel to the cell membrane. Upon return of calcium concentration to baseline levels, absorption anisotropy disappears again (FIG. 9c). Thus, the method of two-photon polarization microscopy described herein allows monitoring conformational changes in a calcium sensitive protein and, thereby, changes in intracellular calcium concentration.

Example 3c

Structure of a Protein Sensitive to Membrane Voltage

Stimuli in neurons are carried by changes in cell membrane voltage. In order to optically monitor cell membrane voltage changes, several different probes based on fluorescent proteins have been developed. One of them is a construct termed VSFP3.1, developed by T. Knopfel (RIKEN Institute, Japan). VSFP3.1 contains a cyan fluorescent protein, whose orientation changes upon a change of membrane voltage. The method of two-photon polarization microscopy described herein has been used to determine that the fluorescent protein in VSFP3.1 is in the resting state oriented in cells such that the long axis of the fluorophore is oriented close to parallel to the cell membrane (FIG. 6e). Changes in membrane voltage lead to changes in VSFP3.1 structure, which can be observed by the method of two-photon polarization microscopy described herein.

Example 3d

Receptor Protein Structure

Properties of extracellular environment, including presence of molecular signals secreted by other cells, are in a cell being detected by membrane receptor proteins. These proteins respond to presence of a particular compound in the extracellular environment by a conformational change with an effect on the intracellular side of the cytoplasmic membrane. A large number of constructs composed of a receptor protein tagged with a fluorescent protein exist, such as the metabotropic glutamate receptor mGluR1-GFP, α2-adrenergic receptor-CFP, or a2-adenosine receptor-YFP. The method of two-photon polarization microscopy described herein has been used to discover (FIG. 6f-6h) that the GFP fluorophore in mGluR1-GFP is oriented almost parallel to the cell membrane; that the CFP fluorophore in α2-adrenergic receptor-CFP is also close to being parallel to the cell membrane, but not as close as the GFP in mGluR1-GFP; and that the fluorophore in a2-adenosine receptor-YFP is close to perpendicular to the cell membrane. Activation of these and other receptor proteins will lead to conformational changes which can, if they lead to changes in orientation of the fluorescent proteins, be observed by the method of two-photon polarization microscopy of the invention.

Example 3e

Structure of Cytoskeletal Proteins

Monitoring of structural properties of proteins by the method of two-photon polarization microscopy of the invention is not limited to membrane proteins, but can also be carried out in proteins attached to other structural support, such as the cytoskeleton. Observations carried out according to the method described herein, on a green fluorescent protein attached through a peptide linker to the tau protein (a natural component of microtubules), show (FIG. 6i) that the long axis of the fluorophore of this green fluorescent protein is oriented close to parallel to the direction of microtubules.

Example 4

Monitoring Protein Function by Observing Changes in Anisotropy

Function of proteins in living cells is often accompanied by changes in protein structure, in interactions with other proteins, or in cellular localization. All of these changes may lead to changes in observed anisotropic properties of fluorescent tags used to label a protein. Thus, the method of obtaining structural information on proteins using polarization fluorescence microscopy described herein can be also used to observe protein function. This is illustrated on an example of monitoring G-protein function, and monitoring function of protein kinase C (PKC).

Example 4a

Monitoring G-Protein Function During Activation by Noradrenaline

According to the current state of knowledge, G-proteins typically exist in cells in a resting state as complexes of three subunits (Gα, Gβ, and Gγ). Activation of a G-protein coupled receptor by an agonist leads to dissociation or reorientation of G-protein subunits. After termination of activation, the trimeric complex of subunits re-forms. This is in agreement with results shown in Example 3a, in which the method of two-photon polarization microscopy described herein was used to determine that, in absence of interactions with Gβ and Gγ subunits, the orientation of the fluorescent protein attached to a Gαi2 subunit is likely disordered. In contrast, in presence of interactions with Gβ and Gγ subunits, the orientation of the fluorescent protein attached to the Gαi2 subunit is to a large extent ordered, such that the long axis of the fluorophore is close to parallel to the cell membrane.

Figure 7:
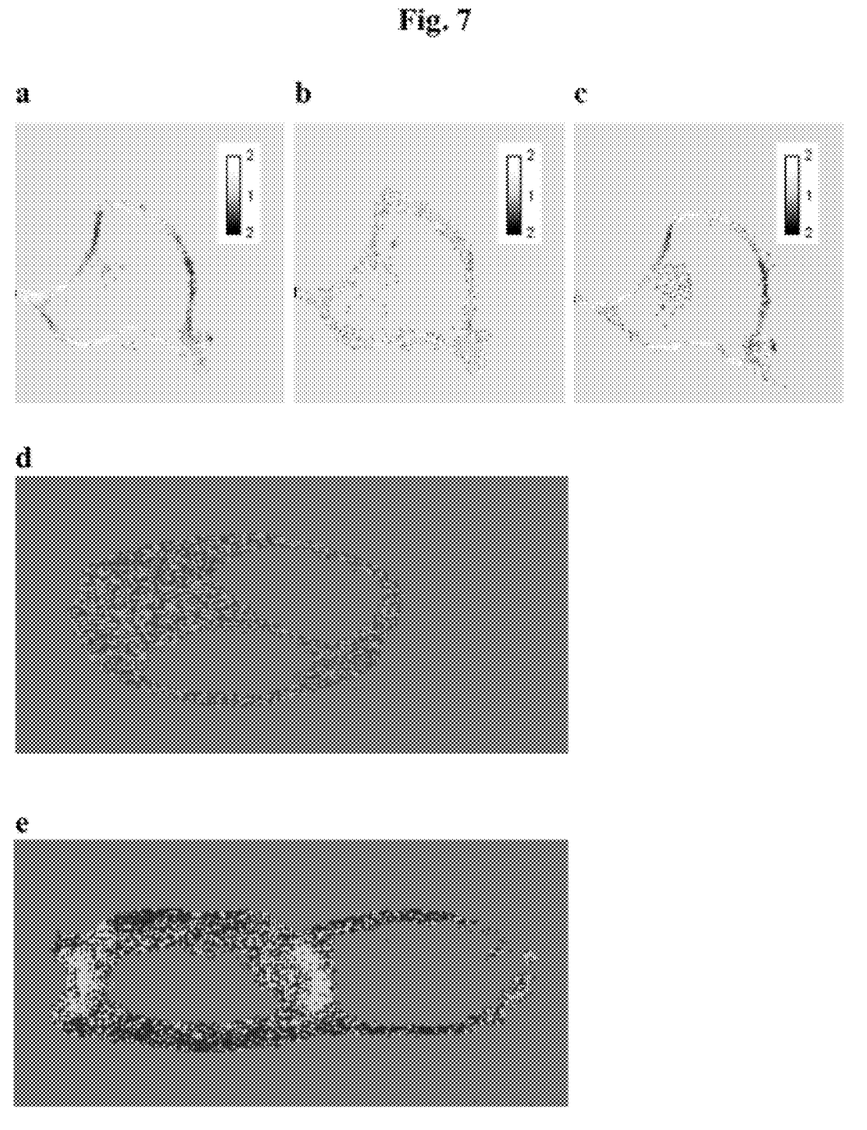
FIG. 7. Examples of applications of the method of two-photon polarization fluorescence microscopy to monitoring physiological processes (G-protein activation, activation of protein kinase C) in live cells. a) A cell expressing G-protein subunits Gαi2-YFP, Gβ1, Gγ2 and an adrenergic receptor, in a resting state, showing absorption anisotropy. b) Same cell as in a), after G-protein activation, with no or little absorption anisotropy present. c) Same cell as in a) and b), after termination of G-protein activation, showing absorption anisotropy again. d) Cells expressing protein kinase C (PKC-RFP) in a resting state show cytoplasmic localization of fluorescence and absence of absorption anisotropy. e) Cells expressing PKC-RFP after activation show membrane localization of fluorescence and absorption anisotropy.

Thus, the extent of observed absorption anisotropy reports on interactions between the Gαi2 subunit with the Gβ1 and Gγ2 subunits, and therefore on function of these G-proteins. FIG. 7 illustrates the ability of the method of the invention to visualize the presence of the trimeric Gαi2-CFP/Gβ1/Gγ2 complex prior to activation of the present receptors (FIG. 7a), dissociation or reorganization of this complex caused by activation of the present adrenergic receptors by noradrenalin (FIG. 7b), and re-formation of this complex upon removal of noradrenalin (FIG. 7c), i.e., changes in functional state of the observed G-protein.

Example 4b

Monitoring Enzyme Activation

Enzymes catalyze chemical reactions in cells. An example of enzymes are so-called kinases, which catalyze phosphorylation reactions in cells. A representative of kinases is protein kinase C (PKC). This kinase is, in a resting state, present in the cytoplasm of a cell. After activation through various signalling cascades, PKC is translocated to the cell membrane and activated. Ability of the method of two-photon polarization microscopy described herein to observe activation of PKC tagged with a red fluorescent protein (RFP) is illustrated in FIG. 7. In a resting state, PKC is localized predominantly to the cytoplasm, orientation of PKC molecules is random, and two-photon absorption anisotropy is not visible (FIG. 7d). After activation by temperature increase, PKC-RFP translocates to the cell membrane, which restricts the present orientations of RFP molecules and causes appearance of anisotropy (FIG. 7e). In the activated state, the long axis of the RFP fluorophore is close to perpendicular to the cell membrane. Thus, the method of two-photon polarization microscopy of the invention allows monitoring of PKC function.

Example 5

Figure 8:
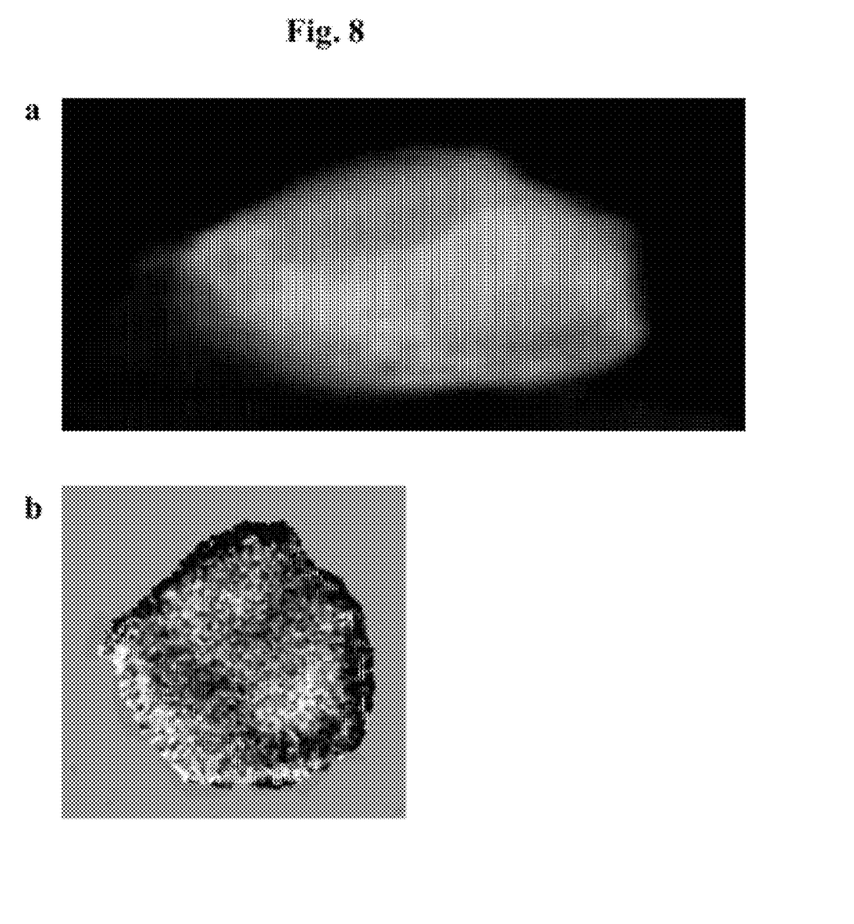
FIG. 8. An example of applications of the method of two-photon polarization fluorescence microscopy to monitoring interactions of cytoplasmic proteins with other molecules. a) A raw mixed image of a cell expressing a fluorescent protein localized to the cytoplasm. b) Same image as in a), but after processing, shows higher depolarization of observed fluorescence in proximity of the cell membrane.

Monitoring Fluorescence Anisotropy as a Reporter of Interactions of a Fluorescently Tagged Cytoplasmic Protein with Other Molecules The method of two-photon polarization microscopy and the device described herein have been used to observe anisotropy of emitted fluorescence of a cytoplasmic yellow fluorescent protein (YFP), expressed in the HEK293 cell line (FIG. 8). The experimental setup was as shown in FIG. 2, except a linear polarizer, oriented horizontally, was placed in front of the fluorescence detector. The excitation beam polarization was alternated between horizontal and vertical between acquisition of consecutive pixels. This lead to presence of alternating lighter and darker columns in the mixed image acquired by the microscope (FIG. 8a). This mixed image was processed similarly to Examples 2 and 3, and the result presented so that darker shades correspond to a lower extent of polarization of the observed fluorescence, and lighter shades correspond to a higher extent of polarization of the observed fluorescence (FIG. 8b). The extent of polarization of emitted fluorescence depends on the lifetime of the excited state of the fluorophore (and therefore on the environment in the vicinity of the fluorophore), on the speed of rotation of the fluorescent molecule (and therefore on its size and interactions with other molecules), and on other phenomena, such as homo-molecular FRET or restrictions of free rotation. The observed lower extent of polarization (i.e., higher de-polarization) of the observed fluorescence in proximity of the cell membrane is indicative of differences in environment in proximity of the cell membrane, as well as of interactions of the fluorescent protein with molecules in the cell membrane or in its immediate vicinity.

Persons skilled in the art will find, or will be able to find, using routine experimental procedures, a number of equivalents to specific embodiments of the invention that are described herein. These equivalents are also included in the scope of the following patent claims.

LIST OF REFERENCE SIGNS USED IN THE FIGURES

B polarizing beamsplitter
C Pockels cell
D driver
G pulse generator
L laser
M microscope
P polarization modulator
R control unit
Z high voltage power supply
1 laser beam
2 timing signals
3 imaging data
4 timing signals
5 low voltage pulses
6 high voltage
7 high voltage pulses

What is claimed is:

1. A method of obtaining structural and functional information about an observed protein based on polarization fluorescence microscopy, the method comprising:
  I) attaching a single fluorophore molecule to a protein to be observed,
  II) subjecting the protein to be observed to two or multiphoton fluorescence microscopy, wherein the protein to be observed is irradiated by a laser beam with polarized light of at least two distinct polarizations, which excites fluorescence from the single fluorophore molecule,
  III) observing at least one fluorescence signal from the single fluorophore molecule and collecting information on localization, intensity and/or polarization of the fluorescence signal excited by the different polarizations of the laser beam,
  IV) observing and quantifying anisotropy of absorption based on the information on localization, intensity, and/or polarization of the fluorescence, and
  V) identifying structural and functional properties of the observed protein based on the observed and quantified anisotropy of absorption.

2. The method of claim 1, wherein the information on localization and intensities of fluorescence excited by different polarizations of the excitation laser beam is obtained in the form of a mixed image, containing in different parts fluorescence intensities excited by different polarizations of the excitation laser beam.

3. The method of claim 2, wherein the processing of the mixed images comprises steps where
  a) for each part of the mixed image, signal elicited by individual polarizations of the excitation beam is identified, and
  b) for each of the used polarizations of the excitation laser beam, a separate image is created, containing signal excited by that polarization.

4. The method of claim 2, wherein the different parts of the mixed image containing fluorescence intensities excited by different polarizations of the excitation laser beam are pixels.

5. The method of claim 4, wherein two different polarizations of the laser beam light are used for excitation.

6. The method of claim 5, wherein the excitation laser beam light polarizations are perpendicular to each other.

7. The method of claim 5, wherein the mixed image contains in odd-numbered pixels intensities of fluorescence excited by one of the two polarizations used, and in even-numbered pixels intensities of fluorescence excited by the other of the two polarizations used.

8. The method of claim 5, wherein the extent of anisotropic properties in individual pixels is determined by calculating the ratio of fluorescence intensity excited with one polarization of the excitation laser beam and fluorescence intensity excited with the other polarization of the excitation laser beam.

9. The method of claim 1, wherein the observed protein is at least one of a membrane protein, a G-protein, a protein sensitive to calcium ion concentration, is a protein sensitive to membrane voltage, a receptor protein, an enzyme, a cytoplasmic protein, or a protein attached to the cytoskeleton.

10. The method of claim 1, further comprising using the information on localization, intensity, and/or polarization of the fluorescence to identify and localize anisotropy of fluorescence.

11. The method of claim 10, further comprising using the localization of anisotropy of fluorescence to identify structural and functional properties of observed protein.

12. The method of claim 9, wherein the observed protein is in a living cell.

* * * * *